US00PP35741P2

(12) United States Plant Patent
Spil

(10) Patent No.: US PP35,741 P2
(45) Date of Patent: Apr. 9, 2024

(54) ***ECHINACEA* PLANT NAMED 'IFECSSPOM'**

(50) Latin Name: *Echinacea hybrida*
Varietal Denomination: IFECSSPOM

(71) Applicant: INNOFLORA PLANT BREEDING B.V., Heerhugowaard (NL)

(72) Inventor: Glenn Spil, Zuidermeer (NL)

(73) Assignee: INNOFLORA PLANT BREEDING B.V., Heerhugowaard (NL)

( * ) Notice: Subject to any disclaimer, the term of this patent is extended or adjusted under 35 U.S.C. 154(b) by 0 days.

(21) Appl. No.: 18/099,957

(22) Filed: Jan. 22, 2023

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ..... A01H 5/02
See application file for complete search history.

(56) References Cited

PUBLICATIONS

CPVO Application Consultation 4.8.16 Citation for 'IFECSSPOM' as per European Community Plant Breeder's Rights application No. 2022/2658; May 24, 2023; 2 pages.*

* cited by examiner

*Primary Examiner* — Kent L Bell
(74) *Attorney, Agent, or Firm* — C. Anne Whealy

(57) ABSTRACT

A new and distinct cultivar of *Echinacea* plant named 'IFECSSPOM', characterized by its upright to broadly upright and relatively compact plant habit; moderately vigorous to vigorous growth habit; freely branching habit; strong dark-colored flowering stems; numerous single-type inflorescences with two whorls of red to red purple-colored ray florets and red-colored receptacle spines; and good garden performance.

2 Drawing Sheets

Figure 1:
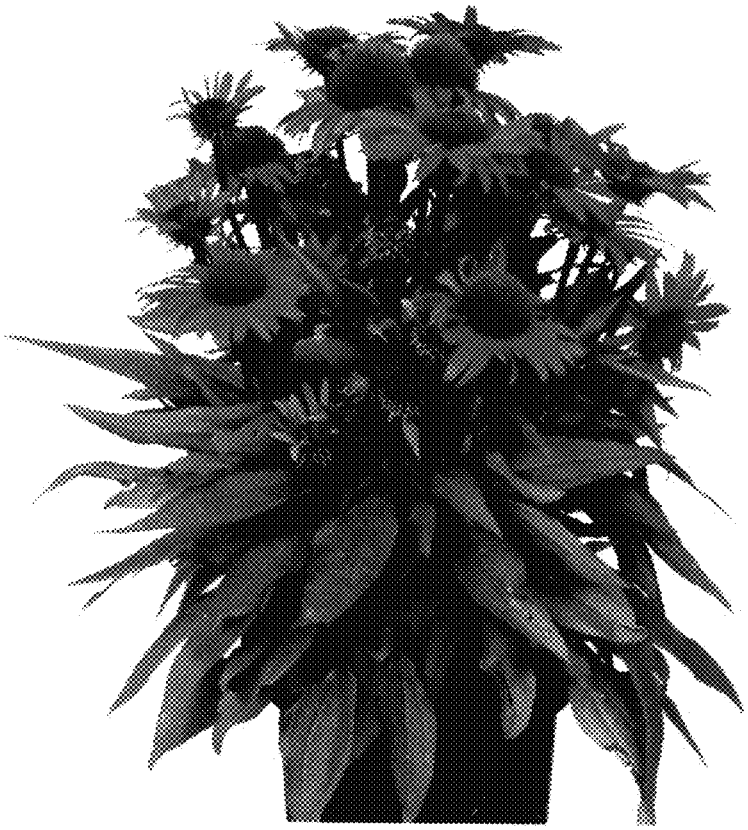

Botanical designation: *Echinacea hybrida.*
Cultivar denomination: 'IFECSSPOM'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Innoflora Plant Breeding B.V. of Heerhugowaard, The Netherlands on Nov. 24, 2022, application number 2022/2658. Foreign priority is not claimed to this application.

BACKGROUND OF THE INVENTION

The present invention relates to a new and distinct cultivar of *Echinacea* plant, botanically known as *Echinacea hybrida*, and hereinafter referred to by the name 'IFECSSPOM'.

The new *Echinacea* plant is a product of a planned breeding program conducted by the Inventor in Heerhugowaard, The Netherlands. The objective of the breeding program is to develop new vigorous and freely flowering *Echinacea* plants with large inflorescences with unique and attractive ray floret coloration.

The new *Echinacea* plant originated from an open-pollination in July, 2017 in Heerhugowaard, The Netherlands of a proprietary selection of *Echinacea hybrida* identified as code number 009-15-K054-03, not patented, as the female, or seed, parent with an unknown selection of *Echinacea*

*hybrida* as the male, or pollen, parent. The new *Echinacea* plant was discovered and selected by the Inventor as a single flowering plant from within the progeny of the stated open-pollination grown in a controlled greenhouse environment in Heerhugowaard, The Netherlands in August, 2018.

Asexual reproduction of the new *Echinacea* plant by in vitro meristem culture in a controlled environment in Heerhugowaard, The Netherlands since September, 2018 has shown that the unique features of this new *Echinacea* plant are stable and reproduced true to type in successive generations.

SUMMARY OF THE INVENTION

Plants of the new *Echinacea* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'IFECSSPOM'. These characteristics in combination distinguish 'IFECSSPOM' as a new and distinct *Echinacea* plant:

1. Upright to broadly upright and relatively compact plant habit.
2. Moderately vigorous to vigorous growth habit.
3. Freely branching habit.
4. Strong dark-colored flowering stems.
5. Numerous single-type inflorescences with two whorls of red to red purple-colored ray florets and red-colored receptacle spines.
6. Good garden performance.

Plants of the new *Echinacea* can be compared to plants of the female parent selection. Plants of the new *Echinacea* differ primarily from plants of the female parent selection in the following characteristics:

1. Plants of the new *Echinacea* are more compact than plants of the female parent selection.
2. Inflorescences of plants of the new *Echinacea* have two whorls of ray florets whereas inflorescences of plants of the female parent selection have a single whorl of ray florets.
3. Ray florets of plants of the new *Echinacea* do not fade as quickly as ray florets of plants of the female parent selection.

Plants of the new *Echinacea* can be compared to plants of *Echinacea purpurea* 'Vintage Red', not patented. In side-by-side comparisons, plants of the new *Echinacea* differ primarily from plants of 'Vintage Red' in the following characteristics:

1. Plants of the new *Echinacea* are more compact than plants of 'Vintage Red'.
2. Plants of the new *Echinacea* are not as freely flowering as plants of 'Vintage Red'.
3. Plants of the new *Echinacea* have larger inflorescences than plants of 'Vintage Red'.

Plants of the new *Echinacea* can also be compared to plants of *Echinacea purpurea* 'Evolution Colorific', not patented. In side-by-side comparisons, plants of the new *Echinacea* differ primarily from plants of 'Evolution Colorific' in the following characteristics:

1. Plants of the new *Echinacea* are more freely flowering than plants of 'Evolution Colorific'.
2. Plants of the new *Echinacea* have larger inflorescences than plants of 'Evolution Colorific'.
3. Ray florets of plants of the new *Echinacea* are red to red purple in color whereas ray florets of plants of 'Evolution Colorific' are pinkish red in color.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet (FIG. 1) is a side perspective view of a typical flowering plant of 'IFECSSPOM' grown in a container.

Figure 2:
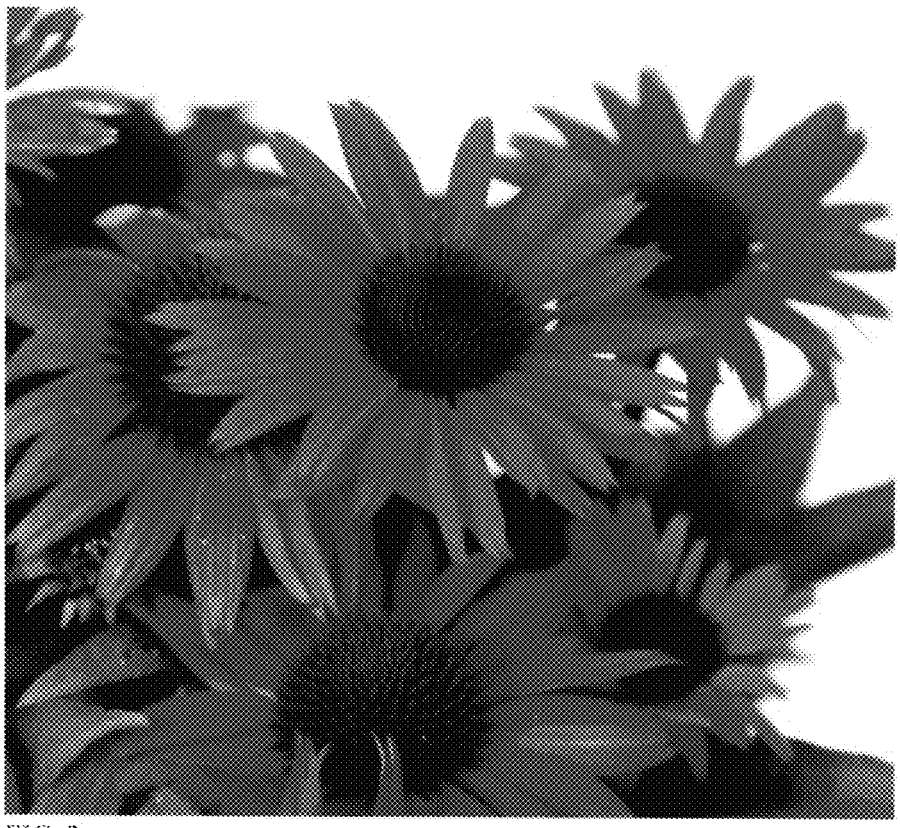

The photograph at the top of the second sheet (FIG. 2) is a close-up view of typical inflorescences of 'IFECSSPOM'.

Figure 3:
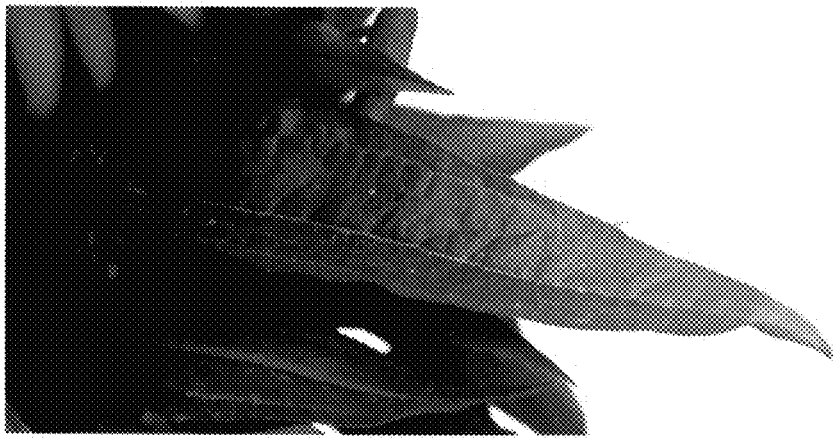

The photograph at the bottom of the second sheet (FIG. 3) is a close-up view of typical leaves of 'IFECSSPOM'.

DETAILED BOTANICAL DESCRIPTION

The aforementioned photographs and following observations and measurements describe plants grown during the late summer in 19-cm containers in an outdoor nursery in Heerhugowaard, The Netherlands and under cultural practices typically used in commercial *Echinacea* production. During the production of the plants, day temperatures ranged from 18° C. to 34° C. and night temperatures ranged from 8° C. to 18° C. Plants were 16 weeks old when the photographs and description were taken. In the following description, color references are made to The Royal Horticultural Society Colour Chart, 2015 Edition, except where general terms of ordinary dictionary significance are used.

Botanical classification: *Echinacea hybrida* 'IFECSSPOM'.

Parentage:

*Female parent*.—Proprietary selection of *Echinacea hybrida* identified as code number 009-15-K054-03, not patented.

*Male parent*.—Unknown selection of *Echinacea hybrida*, not patented.

Propagation:

*Type*.—By in vitro meristem culture.

*Time to initiate roots, summer*.—About twelve days at temperatures about 20° C.

*Time to initiate roots, winter*.—About 16 days at temperatures about 20° C.

*Time to produce a rooted young plant, summer*.—About 36 days at temperatures about 18° C.

*Time to produce a rooted young plant, winter*.—About 42 days at temperatures about 18° C.

*Root description*.—Thick, fleshy; typically white in color, actual color of the roots is dependent on substrate composition, water quality, fertilizer type and formulation, substrate temperature and physiological age of roots.

*Rooting habit*.—Moderately freely branching; sparse.

Plant description:

*Plant form and growth habit*.—Herbaceous perennial; upright to broadly upright and relatively compact plant habit; broadly ovate to broadly oblong in overall shape; freely basal branching habit with about 20 primary lateral branches and about 25 secondary lateral branches developing per plant; moderately vigorous to vigorous growth habit and moderate growth rate.

*Plant height*.—About 38.3 cm.

*Plant diameter or spread*.—About 42.8 cm.

*Lateral branches*.—Length: About 15.2 cm. Diameter: About 5 mm. Internode length: About 2.9 cm. Aspect: Erect to about 17.5° from vertical. Strength: Strong. Texture: Sparsely pubescent; strigose. Color: Surfaces exposed to sunlight, close to N186C and 187A; surfaces shaded from sunlight, close to a blend of 183A and 200B.

Leaf description:

*Basal and cauline leaves*.—Arrangement: Alternate, simple. Length: About 14 cm. Width: About 4 cm. Shape: Narrowly ovate. Apex: Narrowly acute. Base: Short attenuate. Margin: Mostly entire, occasionally sparse to moderate and irregular shallow indentations; slightly and coarsely undulate. Texture and luster, upper surface: Moderately pubescent, strigose and rough; slightly glossy. Texture and luster, lower surface: Moderately pubescent, strigose and rough; matte. Venation pattern: Pinnate. Color: Developing leaves, upper surface: Close to 137A. Developing leaves, lower surface: Close to 146B. Fully expanded leaves, upper surface: Close to NN137A; venation, close to 146C. Fully expanded leaves, lower surface: Close to 147B; venation, close to 146D.

*Petioles, basal and cauline leaves*.—Length: About 3.8 cm. Diameter: About 2.25 mm by 2.5 mm. Texture, upper surface: Smooth, glabrous. Texture, lower surface: Sparsely pubescent. Color, upper surface: Close to a blend of NN137B and 143A; midvein, close to 152D. Color, lower surface: Close to a blend of 137B and 147B; midvein, close to 145A.

Inflorescence description:

*Appearance*.—Single-type inflorescences with ray and disc florets arranged on a capitulum; inflorescences positioned upright above the foliar plane on mostly upright and strong peduncles.

*Flowering habit*.—Freely flowering habit with about 45 developing and fully developed inflorescences per plant.

*Fragrance*.—Moderately fragrant; sweet and pleasant.

*Time to flower*.—Plants flower continuously from late June into late September in The Netherlands.

*Inflorescence longevity*.—Inflorescences maintain good substance for about three weeks on the plant; inflorescences persistent.

*Inflorescence buds*.—Height: About 2.8 cm. Diameter: About 3 cm. Shape: Obovate with flattened apex. Color: Immature involucral bracts, close to between 143A and 146B; immature ray florets, close to N186D; and immature receptacle spines, close to N186C.

*Inflorescence size*.—Diameter: About 10.7 cm. Depth (height): About 3.3 cm. Disc diameter: About 3.5 cm.

*Receptacles*.—Height: About 9 mm. Diameter: About 1.1 cm. Shape: Broadly ovate to close to deltoid. Color: Close to 155C.

*Ray florets*.—Quantity and arrangement: About 29 to 37 arranged in about two whorls at the base of the receptacle. Length: About 4.9 cm. Width: About 1 cm. Shape: Lanceolate to narrowly elliptic; slightly carinate. Apex: Emarginate to praemorse. Base: Cuneate. Margin: Entire. Texture and luster, upper surface: Smooth, glabrous; moderately velvety; matte. Texture and luster, lower surface: Smooth, glabrous; moderately glossy. Aspect: About 30° from horizontal; with development, apices curled slightly downward. Color: When opening, upper surface: Close to a blend of 42A and 179A. When opening, lower surface: Close to 187D. Fully opened, upper surface: Close to a blend of 53A and 60A; venation, similar to lamina color; color becoming closer to 60A and eventually, close to 59B with subsequent development. Fully opened, lower surface: Close to 60C; venation, similar to lamina color; color does not change with subsequent development.

*Disc florets*.—Quantity and arrangement: About 300 per inflorescence, arranged spirally at the center of the inflorescence. Length: About 1.1 cm. Diameter: About 3 mm. Shape: Tubular; proximal 12.5% free, not fused. Apex: Acute. Base: Fused. Margin, free-part: Entire. Texture and luster, inner and outer surfaces: Smooth, glabrous; moderately glossy. Color, when opening, inner and outer surfaces: Apex: Close to 183A. Mid-section: Close to 146B. Base: Close to 145C. Color, fully opened, inner and outer surfaces: Apex: Close to 146C; distally, close to 178B. Mid-section: Close to 145C. Base: Close to 144C.

*Receptacle spines*.—Quantity: One per disc floret; about 300 per inflorescence. Shape: Acicular. Apex: Acute. Base: Attenuate. Texture and luster: Smooth, glabrous; glossy. Color: Apex: Close to N45A. Mid-section: Close to 144A. Base: Close to 144D.

*Involucral bracts*.—Quantity per inflorescence: About 100 arranged in about four whorls. Length: About 1.1 cm. Width: About 3 mm. Shape: Narrowly ovate; close to horizontal to moderately reflexed. Apex: Acute. Base: Cuneate. Margin: Entire. Texture, upper surface: Smooth, glabrous; margins, moderately pubescent. Texture, lower surface: Sparsely pubescent; margins, moderately pubescent. Color, upper surface: Close to 137B. Color, lower surface: Close to 138B.

*Peduncles*.—Length: About 11.2 cm. Diameter: About 4 mm. Strength: Strong. Aspect: Mostly upright. Texture: Moderately pubescent; strigose. Color: Surfaces exposed to sunlight, close to 200B; surfaces shaded from sunlight, close to N199A.

*Reproductive organs*.—Androecium (present on ray and disc florets): Quantity per floret: Five. Filament length: About 3.5 mm. Filament color: Close to 150D. Anther length: About 4 mm. Anther shape: Linear. Anther color: Close to N199A. Pollen amount: Moderate. Pollen color: Close to 17B. Gynoecium (present only on disc florets): Quantity per floret: One. Pistil length: About 6.5 mm. Stigma shape: Decurrent, unequal. Stigma color: Close to N186C. Style length: About 5.5 mm. Style color: Close to 145D. Ovary color: Close to 157C. Seeds and fruits: To date, seed and fruit development have not been observed on plants of the new *Echinacea*.

Pathogen & pest resistance: To date, plants of the new *Echinacea* have not been shown to be resistant to pathogens and pests common to *Echinacea* plants.

Garden performance: Plants of the new *Echinacea* have exhibited good garden performance and to tolerate rain and wind. Plants of the new *Echinacea* have been observed to tolerate high temperatures of about 35° C. and to be hardy to USDA Hardiness Zones 3 to 4.

It is claimed:

1. A new and distinct *Echinacea* plant named 'IFECSS-POM' as illustrated and described.

* * * * *